US00PP23571P2

(12) United States Plant Patent
Kordes

(10) Patent No.: US PP23,571 P2
(45) Date of Patent: Apr. 30, 2013

(54) FLORIBUNDA ROSE PLANT NAMED 'KOR951721'

(50) Latin Name: *Rosa hybrida*
Varietal Denomination: KOR951721

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/136,652

(22) Filed: Aug. 5, 2011

(51) Int. Cl.
*A01H 5/00* (2006.01)

(52) U.S. Cl. ..... Plt./141

(58) Field of Classification Search ..... Plt./141, Plt./142, 150, 151
See application file for complete search history.

*Primary Examiner* — Kent L Bell

(57) ABSTRACT

A new and distinct variety of rose which yields with long lasting hips, which are suitable in floral decorations. It exhibits vigorous growth and an upright, bushy habit. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KOR951721'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1995. The crossing was between a non-patented 'un-named seedling' and a non-patented 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KOR951721'.

SUMMARY OF THE INVENTION

The new rose plant may be distinguished from its seed parent, an 'un-named seedling', by the following combination of characteristics:

1. The hips of 'KOR951721' are hard while the hips from the seed parent are soft.
2. 'KOR951721' has more thorns than the seed parent.

The new rose plant may be distinguished from its pollen parent, an 'un-named seedling' by the following combination of characteristics:

1. 'KOR951721' has a petal count of 5-7 petals while the petal count of the pollen parent is 26-40.

2. The hips of 'KOR951721' form in clusters while the hips of the pollen parent form singly.

The objective of the hybridization was to create a new and distinct rose plant with unique qualities, such as:

1. Uniform growth and flowering;
2. Abundant, long lasting decorative hips;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KOR951721' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KOR951721' was selected in April 1996 from the seedling beds to be asexually propagated for further evaluation. The first asexual propagation of 'KOR951721' was done by budding to seedling understocks in July, 1996 at the inventor's nursery in Offenseth-Sparrieshoop, Germany.

This initial and other subsequent propagations conducted in controlled environments demonstrate that 'KOR951721' reproduces true to type in successive generations of asexual reproduction.

BRIEF DESCRIPTION OF THE DRAWING

The accompanying drawing shows as true as is reasonably possible to obtain in color photographs of this type, the typical characteristics of the buds, flowers, reproductive organs, leaves, and stems of 'KOR951721'.

DETAILED BOTANICAL DESCRIPTION

The following is a description of 'KOR951721', as observed growing in July, 2011 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORcastrav', a rose variety from the same inventor described and illustrated in U.S. Plant Pat. No. 23,091, issued on Oct. 10, 2012, is compared to 'KOR951721' in Chart 1.

CHART 1

| Characteristic | 'KOR951721' | 'KORcastrav' |
|---|---|---|
| Flower bud size upon opening: | 20 mm (l) × 10 mm (w). | 35 mm (l) × 25 mm (w). |
| General Tonality on open flower: | Red-Purple Group N157A. | Red Group 45A. |
| Petaloids: | Absent. | Present. |

Parents:

*Seed parent*.—An 'un-named seedling'.

*Pollen parent*.—An 'un-named seedling'.

Classification:

*Botanical classification*.—*Rosa hybrida* 'KOR951721'.

*Commercial classification*.—Floribunda rose.

FLOWER AND FLOWER BUD

Blooming habit: Recurrent.

Flower bud:

*Size*.—Upon opening, 20 mm in length from base of receptacle to end of bud and 10 mm diameter at its widest point.

*Bud form*.—Short. Pointed ovoid.

*Bud color*.—As sepals first unfold, bud color is Red Group 53D. When ¼ open, the upper surface of petals is Red Group 53D, and the lower surface is Red Group 53D. Guard Petals are Red Group 53C.

*Sepals*.—Color: Upper surface: Green Group 138B. Lower surface: Yellow-Green Group 144A with intonations of Greyed-Purple Group 183C and 183D. Size: Average 18 mm (l)×7 mm (w). Shape: Triangular. Strong foliaceous appendages on three of the five sepals. Apex: Apiculate. Base: Flat at union with receptacle. Quantity: Five. Surface texture: Upper side: Dense pubescence. Lower surface: Slight pubescence. Margins: Dense pubescence with stipitate glands.

Receptacle:

*Surface*.—Mostly Smooth.

*Color*.—Yellow-Green Group 144A with intonations of Greyed-Purple Group 184B.

*Shape*.—Pear-shaped.

*Size*.—8 mm (h)×6 mm (w).

Peduncle:

*Surface*.—With numerous stipitate glands.

*Length*.—20 to 25 mm average length.

*Diameter*.—1.5 to 2.5 mm average diameter.

*Color*.—Yellow-Green Group 146D.

*Strength*.—Moderate.

*Borne*.—Multiple flower buds per stem, generally 15-20.

*Anthocyanin*.—Greyed-Purple Group 183B.

Flower bloom:

*Fragrance*.—None.

*Duration*.—On the plant 3 to 5 days. As a cut flower, 3 to 4 days. Senesced petals drop away cleanly.

*Size*.—Small. When open, the average flower diameter is 35 to 40 mm and the average flower height is 20 mm.

*Form*.—Shape of flower when viewed from the side: Upon opening, upper part: Flat. Upon opening, lower part: Flat. Open flower, upper part: Flat. Open flower, lower part: Convex.

Color:

*Upon opening, petals*.—Outermost petals: Outer Side: Red Group 53B. Inner Side: Red Group 53A. Innermost petals: Outer Side: Red Group 53B. Inner Side: Red Group 53A.

*Upon opening, basal petal spots*.—Basal petal spot, outermost petals: Outer Side: Green-Yellow Group 1D. Inner Side: Yellow Group 2A. Basal petal spot, innermost petals: Outer Side: Yellow Group 3B. Inner Side: Yellow Group 6A.

*After opening, petals*.—Outermost petals: Outer Side: Red-Purple Group 59C. Inner Side: Red Group 53B. Innermost petals: Outer Side: Red-Purple Group 59C. Inner Side: Red Group 53B.

*After opening, basal petal spots*.—Basal petal spot, outermost petals: Outer Side: Green-Yellow Group 162B. Inner Side: Green-Yellow Group 162B. Basal petal spot, innermost petals: Outer Side: Green-Yellow Group 162B. Inner Side: Green-Yellow Group 162B.

General tonality: On open flower Red-Purple Group N157A. No change in the general tonality at the end of the 3$^{rd}$ day. Afterwards, general tonality is Red-Purple Group 66A and Red-Purple Group 65D.

Petals:

*Petal count*.—Average Range: Approximately 5 petals under normal conditions.

*Petal reflex*.—Petals reflex slightly.

*Petal edge*.—Variable. Entire to slightly lobed.

*Petal shape*.—Deltoid. Apex shape is pointed obtuse. Shape of base is acute.

*Petal size*.—20-23 mm (l)×20-23 mm (w).

*Thickness*.—Thin.

*Petal arrangement*.—Generally in a regular pattern with overlapping edges.

Petaloids: Absent.

Reproductive organs:

*Pistils*.—Approximately 20 present. Stigmas: Location: Slightly superior in position to anthers. Color: Yellow-Green Group 1C. Styles: Length: About 4 mm long. Color: Yellow-Green Group 1D.

*Stamens*.—Approximately 120 on average and regularly arranged. Anthers: Size: 1.5 mm long, on average. Pollen: Generally present. Color: Greyed-Orange Group 163A. Filaments: Color: Yellow Group 6A. Length: About 5 mm.

THE PLANT

Growth: Vigorous.

Plant habit: Upright to bushy habit. When grown as a budded field grown plant, the average plant height is 80-100 cm and the average plant width is 60-80 cm.

Stems:

*Stem color*.—Young wood: Yellow-Green Group 144A. Older wood: Yellow-Green Group 144A.

*Stem surface*.—Young wood: Smooth. Older wood: Smooth.

Prickles: Present.

*Incidence*.—Older stems: Few to none. Young wood: 25 per 10 each cm of stem, on average.

*Size*.—Average length: 10 mm.

*Color*.—Immature prickles: Greyed-Purple Group 184B. Mature prickles: Greyed-Purple Group 184B.

*Shape*.—Concave.

Leaves and leaflets: Normally 7 leaflets on normal leaves in middle of the stem.

*Venation pattern*.—Pyramidal net pattern.

*Leaf size*.—130 mm (l)×100 mm (w).

*Abundance*.—Average.

*Texture*.—Leathery. Upper side of leaflet: Semi-glossy. Under side of leaflet: Matte.

*Color, mature foliage*.—Upper Leaf Surface: Yellow-Green Group 147A. Lower Leaf Surface: Green Group 138B.

*Color, juvenile foliage*.—Upper Leaf Surface: Yellow-Green Group 146A. Lower Leaf Surface: Green Group 143B.

*Anthocyanin intonation*.—Present on juvenile leaf margins, veins, and underside. Color is Greyed-Purple Group 187A.

Stipules:

*Size*.—Distance between tips is 20 mm long, on average.

*Stipule color*.—Green Group 144A.

*Anthocyanin*.—Greyed-Red Group 181B.

*Stipitate glands*.—Present.

*Margins*.—Very ciliated with stipitate glands.

*Shape*.—Apex: Apiculate. Base: Winged.

Petiole:

*Length*.—About 25 mm.

*Diameter*.—About 2 mm.

*Petiole color*.—Yellow-Green Group 144A.

*Underneath*.—Smooth.

*Margins*.—With stipitate glands.

*Anthocyanin*.—Greyed-Red Group 181A.

*Prickles*.—Absent.

Petiole rachis:

*Length*.—40-45 mm, on average.

*Diameter*.—1.5 mm, on average.

*Color*.—Yellow-Green Group 144A.

*Underneath*.—Mostly smooth, with limited numbers of prickles and stipitate glands.

*Margins*.—With stipitate glands.

*Anthocyanin*.—Intonations of Greyed-Red Group 181A present on juvenile tissue.

*Prickles*.—Present. Approximately 4-8 per leaf.

Leaflets:

*Size*.—Average size of the terminal leaflet is 40-45 mm (l)×30-35 mm (w).

*Shape*.—Entire leaflet: Ovate. Base: Obtuse. Apex: Acute.

*Margins*.—Finely serrated.

*Texture*.—Leathery.

Hips/seed formation: Numerous hips in sprays. Average size is 10 mm (l)×10 mm (w). Initially, Yellow-Green Group 144A. Color of Greyed-Red Group 180A when mature.

Winter hardiness: To date, the variety has been grown successfully in Zones 5 to 9.

Disease resistance: Excellent resistance to powdery mildew (*Sphaerotheca pannosa*), rust (*Phragmidium* sp.), and blackspot (*Diplocarpon rosae*) diseases under normal growing conditions.

Other comments: Cultivar produces sprays of hips which are suitable for use in floral decoration.

I claim:

1. A new and distinct variety of rose plant, as described and illustrated herein.

* * * * *

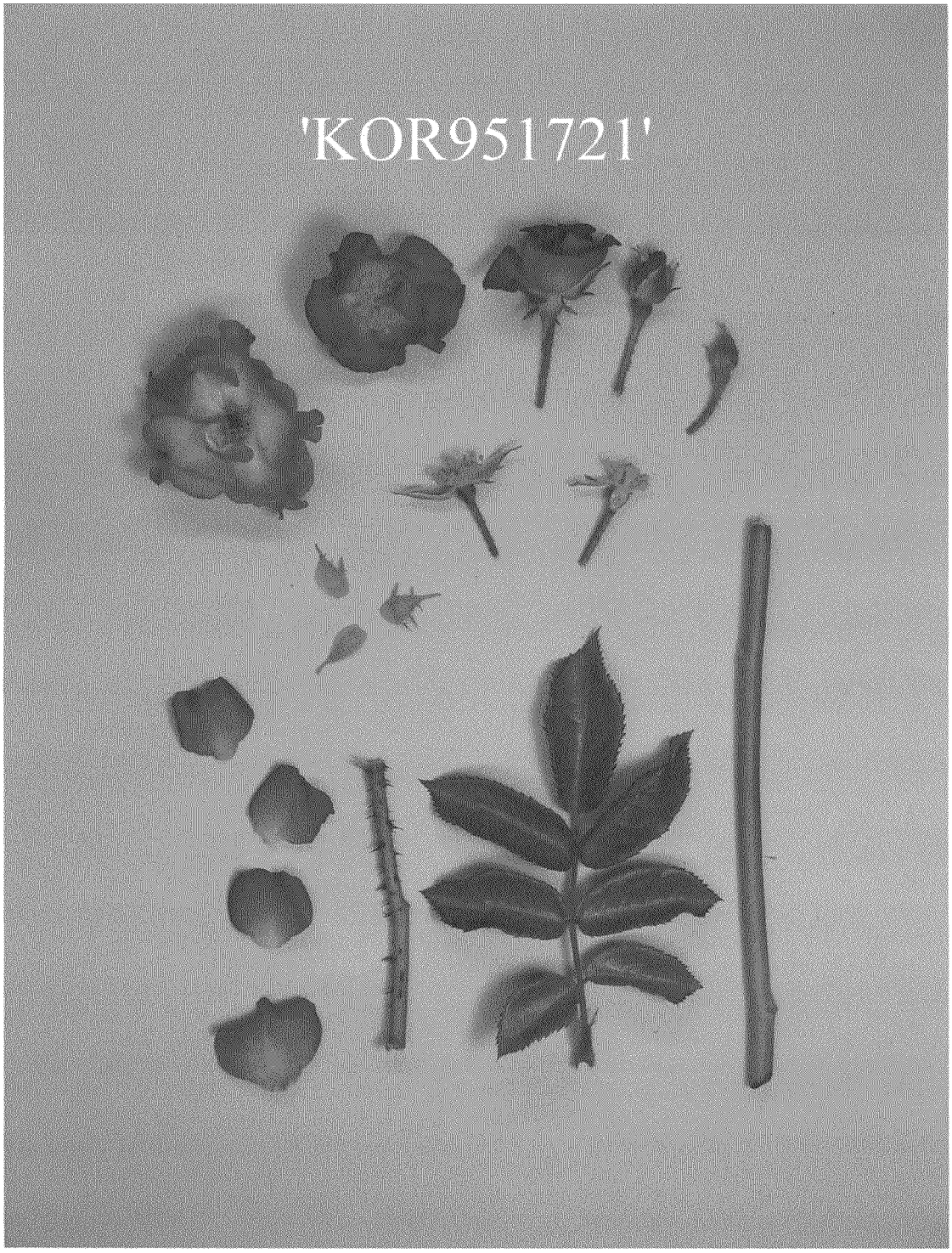
'KOR951721'